United States Patent
Zhao et al.

(10) Patent No.: US 10,968,470 B2
(45) Date of Patent: Apr. 6, 2021

(54) METHOD FOR PREPARING RUBUSOSIDE (71) Applicant: Guilin Layn Natural Ingredients Corp., Guilin (CN)

(72) Inventors: Jun Zhao, Guilin (CN); Yunfei Song, Guilin (CN); Wenguo Yang, Guilin (CN); Linfeng Zhang, Guilin (CN); Meiying Yang, Guilin (CN); Yuyu Li, Guilin (CN)

(73) Assignee: Guilin Layn Natural Ingredients Corp., Guilin (CN)

( * ) Notice: Subject to any disclaimer, the term of this patent is extended or adjusted under 35 U.S.C. 154(b) by 0 days.

(21) Appl. No.: 16/316,124

(22) PCT Filed: Sep. 14, 2017

(86) PCT No.: PCT/CN2017/101709
§ 371 (c)(1),
(2) Date: Jul. 21, 2020

(87) PCT Pub. No.: WO2018/233092
PCT Pub. Date: Dec. 27, 2018

(65) Prior Publication Data
US 2020/0340027 A1  Oct. 29, 2020

(30) Foreign Application Priority Data
Jun. 19, 2017  (CN) .......................... 201710465808.0

(51) Int. Cl.
*C12P 19/44* (2006.01)
*C12P 17/16* (2006.01)
*C12N 1/22* (2006.01)

(52) U.S. Cl.
CPC ................ *C12P 17/16* (2013.01); *C12N 1/22* (2013.01); *C12P 2201/00* (2013.01)

(58) Field of Classification Search
CPC ...................................................... C12P 17/16
See application file for complete search history.

(56) References Cited

U.S. PATENT DOCUMENTS

2015/0118379 A1\* 4/2015 Markosyan ............. C12P 19/14
426/548

FOREIGN PATENT DOCUMENTS

| CN | 102702284 A | 10/2012 |
|---|---|---|
| CN | 102838644 A | 12/2012 |
| CN | 104193788 A | 12/2014 |
| CN | 104262425 A | 1/2015 |
| CN | 104926892 A | 9/2015 |
| CN | 105061526 A | 11/2015 |
| CN | 106243165 A | 12/2016 |
| CN | 106632540 A | 5/2017 |
| CN | 101112458 A | 1/2018 |

OTHER PUBLICATIONS

Zhao, Y. "The Key of Technologies for Extraction and Preparation of Traditional Chinese Medicine and Natural Products" (2012); 9 pgs.

\* cited by examiner

*Primary Examiner* — Bin Shen
(74) *Attorney, Agent, or Firm* — Fox Rothschild LLP (57) ABSTRACT

The application provides a method for preparing rubusoside comprising steps of raw material crushing, flash extraction, double centrifugations, macroporous resin purification, desorption, enzymatic hydrolysis, organic film decoloring, concentration, crystallization and drying. The application optimizes the quality control of key process such as extraction, separation, purification and decolorization, and can obtain the rubusoside product with purity more than 99%, and the product is white, no bitterness, less solvent residue, no pesticide residue, and stable quality.

9 Claims, 6 Drawing Sheets

METHOD FOR PREPARING RUBUSOSIDE

TECHNICAL FIELD

The application belongs to the technical field of plant extraction, and in particular relates to a method for preparing rubusoside.

BACKGROUND TECHNIQUE

Sweet tea (*Rubus suatrssimus S. Lee*) is one of the four famous products in Guangxi, and is also grown in Guangdong, Hunan, Jiangxi and other provinces. It contains a large amount of bioflavonoid. In addition to the effect of ordinary green tea, it also has the effects such as preventing and treating cardiovascular diseases, preventing stroke, preventing cancers, and preventing dental diseases, and thus it has extremely high medicinal value.

Rubusoside is the main ingredient in Sweet tea that contributes to the sweetness and health effects. The previous method for extracting rubusoside is simple by the use of hot water extraction. Although the method is simple, the extraction rate is often very low, resulting in great resource waste. In order to improve the extraction rate and product quality, some studies have been done in recent years on the improvement of the rubusoside extraction process.

For example, CN106243165A discloses a method for extracting rubusoside from leaves of Sweet tea, comprising the following steps: 1) crushing leaves of Sweet tea, extracting using ethanol, filtering the extract solution, and recovering ethanol from the filtrate under reduced pressure to obtain a crude extract; 2) dissolving the crude extract in water, filtering, and taking the filtrate for use; 3) passing the filtrate of step 2) through high-molecular filtration membrane with the molecular weight cutoff of 1000 for separation, and collecting the effluent; 4) adding to the effluent $EuAlO_3$ at a ratio of 1000 ml:0.2 to 1 mg, precipitating for 30 to 50 s, removing precipitate via filtration, and drying the filtrate to obtain rubusoside.

CN104926892A discloses a method for extracting rubusoside from Sweet tea, comprising the following steps: (1) crushing leaves of Sweet tea; (2) pretreating by ultrasonic crushing; (3) extracting at a constant temperature; (4) filtrating and collecting filtrate; (5) flocculating the obtained filtrate at pH 10 and 60° C. using $FeSO_4$ as the flocculating agent; (6) eluting on a macroporous adsorption resin using distilled water as the eluent, and collecting the effluent; (7) concentrating the effluent; (8) adding methanol into the concentrate solution obtained in step (7), crystallizing at a low temperature, and centrifuging to recover methanol; (9) drying the solid material isolated after centrifugation under vacuum at 45° C. to 50° C. to a constant weight to obtain rubusoside.

The common problems met in the practical production of the domestic rubusoside extraction industry including those mentioned above, are the complex process, poor control of the key production processes and the introduction of harmful chemical components, making the product having different degrees of bitterness, not white enough, and unstable quality.

SUMMARY OF THE INVENTION

In order to solve the problems existing in the prior art and to prepare high-quantity and high-quality rubusoside, the inventors optimized the quality control of key steps such as extraction, separation, purification and decolorization, and provides a method for preparing rubusoside.

A specific technical solution of the present application is: a method for preparing rubusoside, comprising the steps:

(1) providing a dry sample of Sweet tea leaves, crushing and passing them through 40-60 mesh sieve, putting the obtained powder material into a flash extractor, in which water at the amount of 18-20 times by weight of the powder is added, extracting for 3 times, 1 minute for each time, and combining all extract solutions to get the total extract solution;

(2) concentrating the total extract solution to a concentrate solution 5 times by weight of the raw leaves, centrifuging the concentrate solution through a disc centrifuge and a tube centrifuge to obtain a centrifugate, and adjusting the centrifugate to pH 5.0-6.0 using an acid solution;

(3) passing the adjusted centrifugate through a macroporous resin column, adjusting the effluent to pH 7.0 using 0.2% sodium hydroxide solution, detecting the content of rubusoside and ending sample loading when the content is >1%; when the loading is completed, washing the column firstly using pure water until the effluent is colorless and clear, secondly using alkaline solution until the effluent is PH 11 to 12, thirdly using pure water until the effluent is PH 7.0-7.5, fourthly using an acid solution until the effluent is PH 2.0-2.5, and finally using water until the effluent is PH 7.0;

(4) desorbing by 45%-50% ethanol solution, collecting the effluent from the time rubusoside is detected as >1% to the time rubusoside is detected as <1%, and concentrating the effluent under reduced pressure to a concentrate solution of 5 Baume Degrees (°Bé);

(5) adding a biological enzyme to the concentrate solution obtained in step (4), and digesting at a temperature of 45-60° C. for 1-3 hours to obtain an enzymatic hydrolysate;

(6) passing the enzymatic hydrolysate through an organic membrane of 8000 molecular weight under the inlet pressure of 0.45-0.5 MPa, then through an organic membrane of 800 molecular weight under the inlet pressure of 1.8-2.0 MPa to obtain a decolored filtrate;

(7) concentrating the filtrate under reduced pressure to obtain a thick paste of 15 Baume Degrees (°Bé), adding methanol or ethanol as a solvent at an amount 3 times that of the thick paste, crystallizing at 5-11° C. for 8-14 hours, drying the obtained crystal to obtain rubusoside.

Wherein:

The centrifugation time in the disc centrifuge described in step (2) is 30-50 minutes, and the centrifugation time of the tube centrifuge is 40-60 minutes.

The alkaline solution in step (3) is a 0.2% aqueous solution of sodium hydroxide or 0.2% aqueous solution of potassium hydroxide; and the acid solution is 0.4% aqueous solution of hydrochloric acid or 0.45% aqueous solution of sulfuric acid.

The macroporous resin column in step (3) is one selected from T-28 resin or H-30 resin.

The biological enzyme in step (5) is selected from one or a combination of two or more of bromelain, pectinase and neutral protease.

Preferably, the amount of the biological enzyme added in step (5) is 0.5‰-1.0‰ of the total weight of the leaves.

Preferably, the amount of the biological enzyme added in step (5) is 0.6‰-0.8 of the total weight of the leaves.

Preferably, the biological enzyme in step (5) is a combination of pectinase and neutral protease at the ratio of 5:1.

Preferably, the biological enzyme in step (5) is a combination of pectinase and bromelain at the ratio of 1:1.

Preferably, the biological enzyme in step (5) is a combination of a neutral protease and bromelain at the ratio of 4:1.

Compared with the prior art, the present application has the following features and technical effects.

1. The total extract solution of Sweet tea leaves is obtained by flash extractor, which greatly improves the production efficiency compared with the traditional extraction tank, and it can be operated at normal temperature and easily.

2. For the extract solution obtained by flash extraction, a two-stage centrifuge process using a disc centrifuge and a tube centrifuge ensures the maximum removal of impurities.

3. In the purification using macroporous resin column, the column is washed five times using "water-alkaline solution-water-acid solution-water" sequentially, and the various parameters of the macroporous resin purification are optimized.

4. The combination of enzymatic hydrolysation and organic membrane is used to replace resin decolorization. The content of rubusoside is 5% higher than the case where resin decolorization is used. The product obtained by crystallization is snow white, and has no bitterness, little solvent residue, and no pesticide residue.

EMBODIMENTS

Example 1

(1) 1.5 kg dried leaves of Sweet tea was taken, and the content of rubusoside was 5.3% according to HPLC. The dried leaves were crushed through 40 mesh sieve. The obtained material was put into a flash extractor. Pure water was used as the extraction solvent. Into the material, water at the amount of 18 times by weight of the material was added. The rotation rate was 5000 R/min. The extraction was carried out at room temperature for 3 minutes, one minute for each time and three times in total, a 2 minute-break between two extractions. The filtrates from three extractions were separated and combined to obtain a total filtrate.

(2) The total filtrate was concentrated to a concentrate solution 5 times by weight of the raw leaves. The concentrate solution was cooled to 25° C., and centrifuged in a disc centrifuge for 45 minutes and then in a tube centrifuge for 60 minutes. The centrifugal deposit was discarded and the centrifugate was adjusted to pH=5.2 with acid solution.

(3) The adjusted centrifugate in step (2) was passed through a macroporous resin column (T-28 resin). The effluent was adjusted to pH=7.0 using 0.2% sodium hydroxide solution. The loading into the column was ended when the content of rubusoside was detected as >1%. After the loading, the column was firstly washed using pure water until the effluent was colorless and clear, secondly using alkaline solution until the effluent was PH 11, thirdly using pure water until the effluent was PH 7.1, fourthly using an acid solution until the effluent was PH 2.0, and finally using water until the effluent was PH 7.0.

(4) Desorption was carried out with 48% ethanol. The effluent was collected from the time the rubusoside was detected as >1% to the time rubusoside was detected as <1%. Ethanol was removed from the collected effluent by concentrating under reduced pressure, and a concentrate solution of 5 Baume Degrees (°Bé) was obtained.

(5) The concentrate solution obtained in step (4) was added to 0.96 g bromelain, and was digested at 48° C. for 3 hours, and the obtained solution was allowed to cool to a normal temperature of 25° C. to obtain an enzymatic hydrolyzate.

(6) The enzymatic hydrolyzate was passed through an organic membrane of 8000 molecular weight under the inlet pressure of 0.45 MPa, then through an organic membrane of 800 molecular weight under the inlet pressure of 1.8 MPa, to obtain the decolored filtrate.

(7) The filtrate was concentrated under reduced pressure to obtain a thick paste of 15 Baume Degrees (°Bé). A solvent at an amount 3 times that of the thick paste was added, stirred thoroughly and crystallized at 6° C. for 12 hours. The obtained crystal was dried to obtain 77.1 g rubusoside. According to HPLC, the content of rubusoside was 99.3%.

Examples 2-8

On the basis of the method described in Example 1, the combination of various enzymes, the temperature and time for the enzymatic hydrolysis, the first organic film (inlet pressure), the second organic film (inlet pressure), the temperature and time for crystallization and the like were adjusted. The quality and the content of the prepared rubusoside were determined by HPLC. The results are shown in Table 1.

In order to verify that the present application has outstanding technical effects, the inventors conducted four comparative experiments as follows.

Comparative Example 1

The rubusoside was extracted using the method of example 1 except that the extraction device used in step (1) was replaced by an extraction tank.

Specifically, the method for extracting rubusoside using the extraction tank was as follows. 1.5 kg dried leaves of Sweet tea was taken, and the content of rubusoside was 5.4% according to HPLC. The dried leaves were crushed through 40 mesh sieve. The obtained material was put into an extraction tank. Distilled water at the amount of 8 times by weight of the material was added, and the extraction was carried out for 3 times, one hour for each time. The filtrates from three extractions were separated and combined to obtain a total filtrate.

Comparative Example 2

The rubusoside was extracted using the method of example 1 except that the centrifugation in step (2) was carried out once using a table-top high speed centrifuge.

Specifically, the method for extracting rubusoside using a table-top high speed centrifugator was as follows. The total filtrate was concentrated to the amount five times that of the raw leaves. The obtained concentrate solution was cooled to 25° C., and centrifuged in a table-top high speed centrifuge for 60 minutes. The centrifugal deposit was discarded and the centrifugate was adjusted to pH 5.2 using an acid solution.

Comparative Example 3

The rubusoside was extracted using the method of example 1 except that the macroporous resin column purification in step (3) and the desorption in step (4) were carried out using national routine processes.

Specifically, the macroporous resin column purification and the desorption were as follows. The filtrate with the adjusted pH value was loaded into the macroporous resin column until the effluent was no sweet. The column was washed using distilled water until the effluent was colorless and clear. Desorption was carried out with 60% ethanol from the time there was a sweet taste to the time the sweet taste was gone. A concentrate solution of 5 Baume Degrees (°Bé) was obtained.

Comparative Example 4

The rubusoside was extracted using the method of example 1 except that steps (5) and (6) were omitted so that the concentrate solution was directly subjected to crystallization.

The rubusoside prepared in Example 1 was compared to those obtained in Comparative Examples 1-4 in terms of quality, recovery rate, content and color. The results are shown in Table 2.

According to the data in Examples 1-8 and Comparative Examples 1-4 in Table 1 and Table 2, the following can be concluded.

1. All the parameters involved in the present application may be adjusted within the feasible ranges and the obtained rubusoside all has a content of more than 99% with slight fluctuation, indicating that the method of the present application is reliable and can better control the product quality.

2. Extraction process, separation process, macroporous resin column purification, desorption process, crystallization temperature and crystallization time have great influence on the yield of rubusoside. The flash extraction process, the two-stage extraction process and the optimization of the macroporous resin purification have an outstanding contribution to the recovery rate of rubusoside.

3. The type or combination of enzymes, enzymatic hydrolysis parameters, and process parameters of organic membranes have a great influence on the color of rubusoside. The "enzymatic hydrolysis+organic film" decolorization process adopted by the application has an outstanding contribution to the improvement of whiteness of the product.

TABLE 1

Process technical parameters and product test results of Examples 2-8

Figure 1:
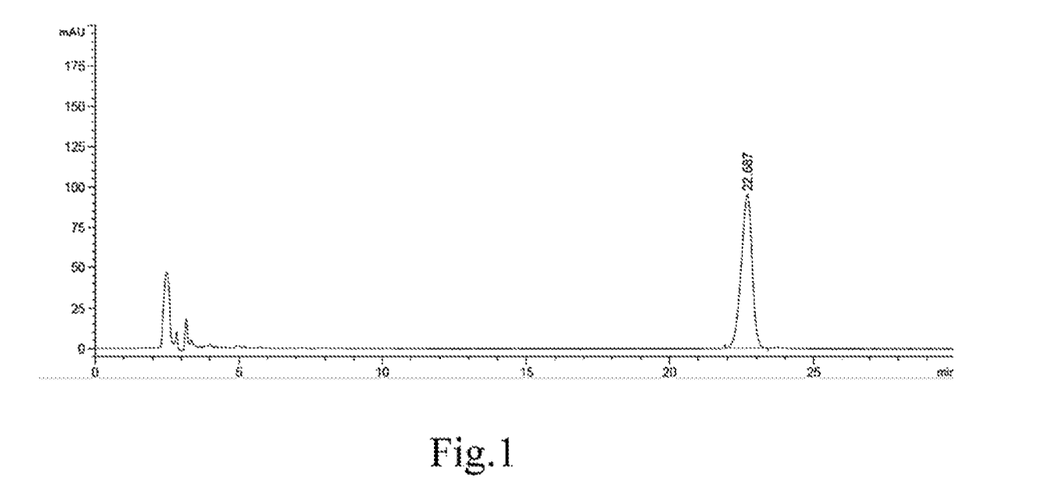
FIGS. 1-8 are HPLC profiles of the rubusoside products prepared in Examples 1-8, respectively.
Figure 2:
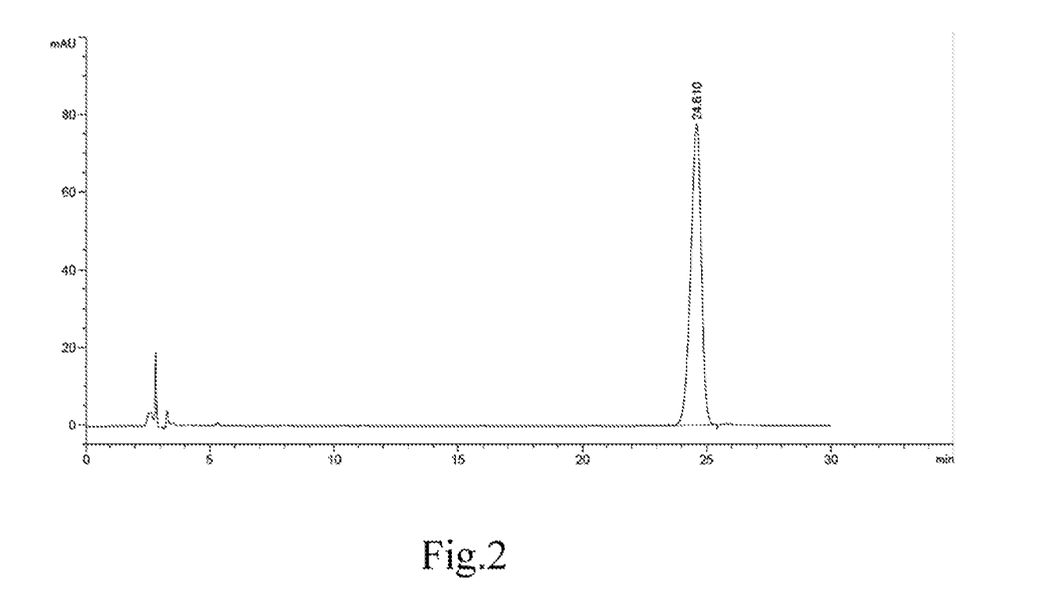
Figure 3:
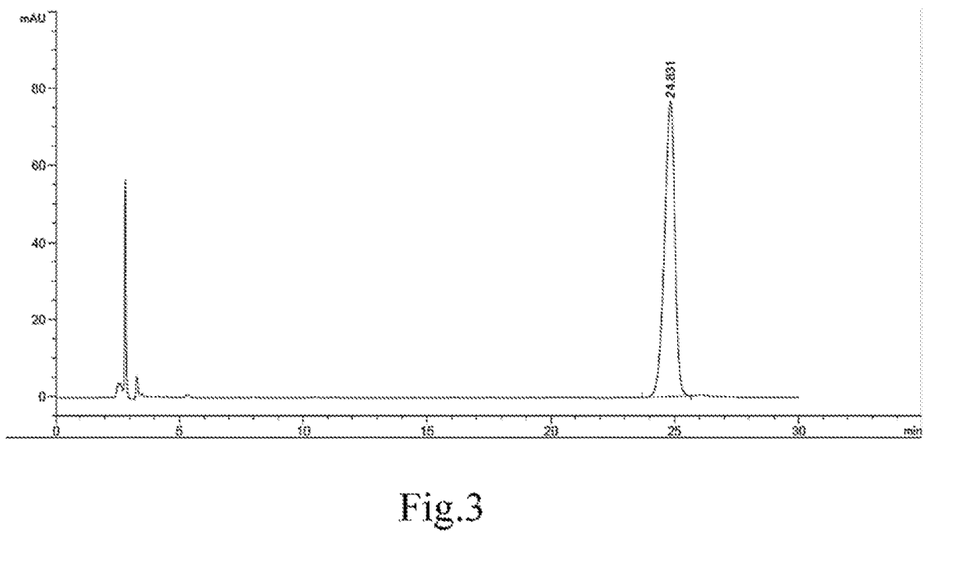
Figure 4:
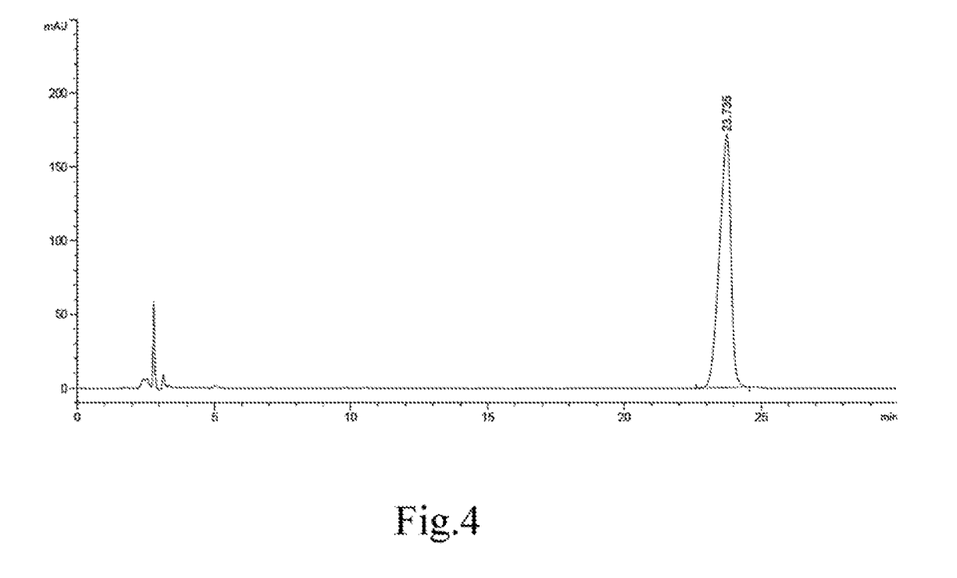
Figure 5:
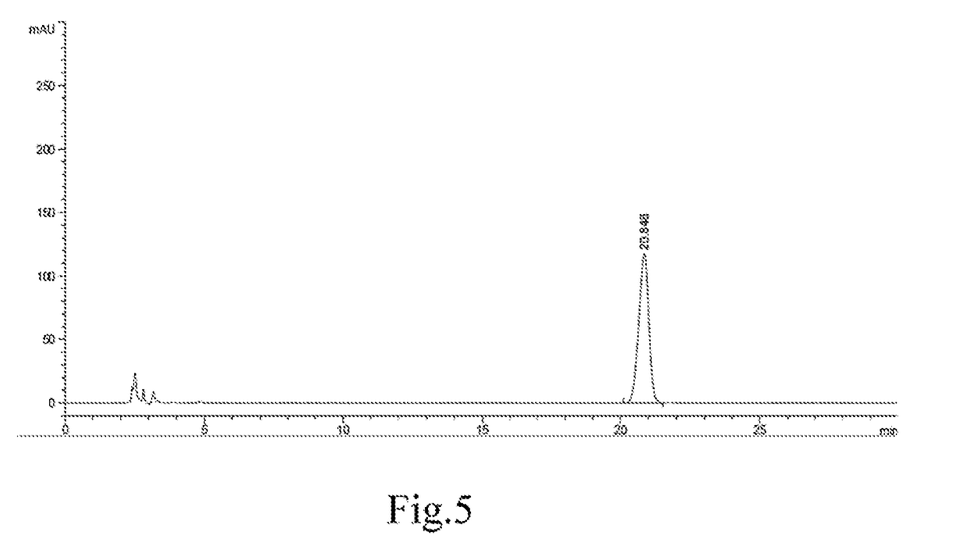
Figure 6:
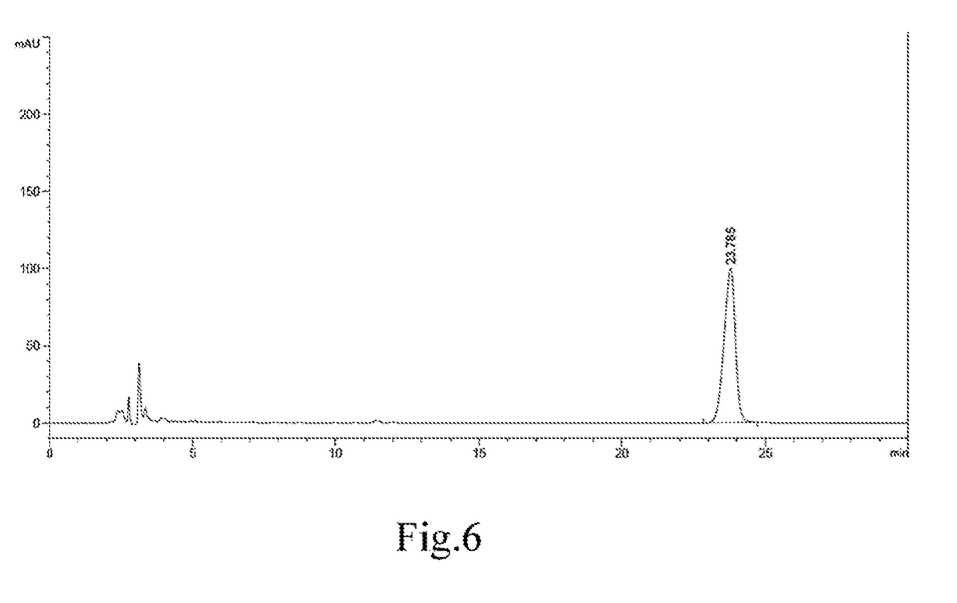
Figure 7:
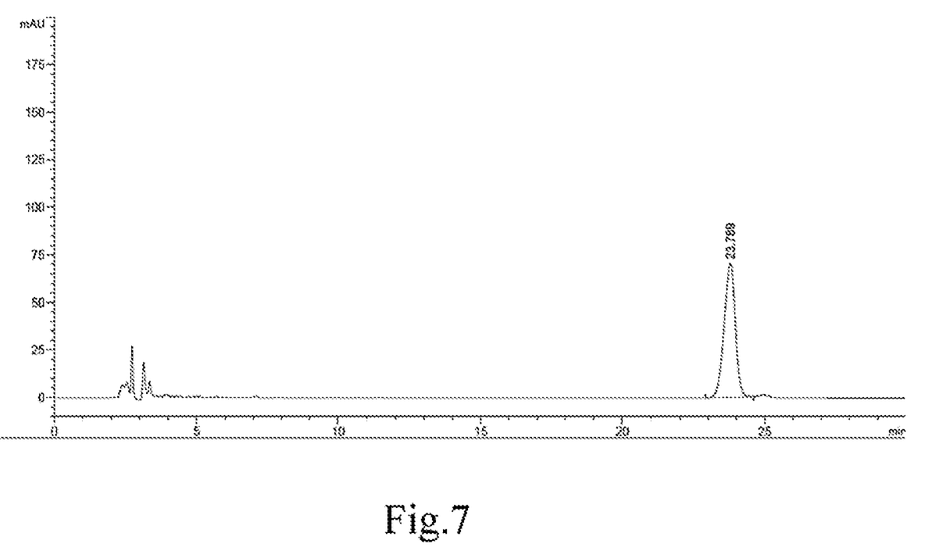
Figure 8:
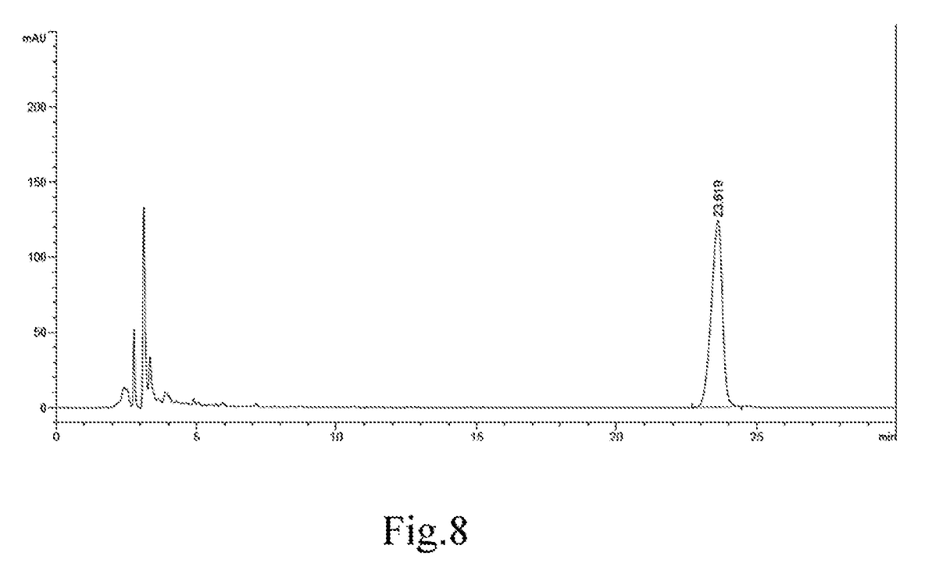

| parameters | Example 1 | Example 2 | Example 3 | Example 4 | Example 5 | Example 6 | Example 7 | Example 8 |
|---|---|---|---|---|---|---|---|---|
| Raw material (dried leaves)/kg | 1.5 | 1.5 | 1.5 | 1.5 | 1.5 | 1.5 | 1.5 | 1.5 |
| Rubuscoside content in the raw material (HPLC)/% | 5.3 | 5.5 | 5.4 | 5.3 | 5.2 | 5.3 | 5.5 | 5.4 |
| Enzymes | Bromelain | Pectinase | Neutral protese | Bromelain | Neutral protese | Pectinase:Neutral protese = 5:1 | Pectinase:Bromelain = 1:1 | Neutral protese:Bromelain = 4:1 |
| Enzyme amount/g | 0.96 | 1.0 | 0.98 | 0.96 | 0.95 | 1.0 g + 0.2 g | 0.5 g + 0.5 g | 1.0 g + 0.25 g |
| Temperature for enzymatic hydrolysis/° C. | 45 | 55 | 48 | 60 | 48 | 48 | 48 | 48 |
| Time for enzymatic hydrolysis/h | 3 | 3 | 1 | 2 | 3 | 3 | 3 | 3 |
| Inlet pressure for the first organic membrane/Mpa | 0.45 | 0.45 | 0.45 | 0.5 | 0.45 | 0.45 | 0.5 | 0.45 |
| Inlet pressure for the second organic membrane/Mpa | 2.0 | 1.8 | 2.0 | 1.8 | 1.8 | 1.8 | 1.8 | 2.0 |
| Crystallization temperature/° C. | 5 | 6 | 6 | 8 | 6 | 6 | 6 | 7 |
| Crystallization time/h | 12 | 8 | 8 | 8 | 12 | 12 | 10 | 12 |
| Rubuscoside product/g | 77.5 | 80.58 | 78.6 | 77.9 | 76.1 | 77.1 | 79.8 | 78.8 |
| Rubuscoside recovery rate/% | 96.61 | 96.89 | 96.36 | 97.20 | 96.98 | 96.30 | 95.86 | 96.51 |
| Rubuscoside content (HPLC)/% | 99.1% (FIG. 1) | 99.2% (FIG. 2) | 99.3% (FIG. 3) | 99.2% (FIG. 4) | 99.4% (FIG. 5) | 99.3% (FIG. 6) | 99.1% (FIG. 7) | 99.2% (FIG. 8) |
| Visual whiteness comparison | Example 8 > Example 5 > Example 6 > Example 3 > Example 7 > Example 1 > Example 2 > Example 4 | | | | | | | |

TABLE 2

Product Comparison of Example 1 and Comparative Examples 1-4

Figure 9:
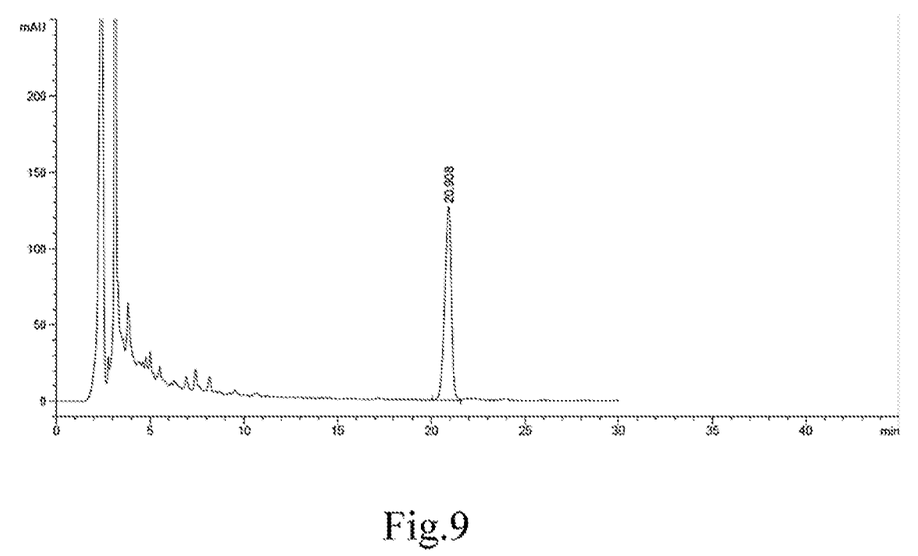
FIGS. 9-12 are HPLC profiles of the rubusoside products prepared in Comparative Examples 1-4, respectively.
Figure 10:
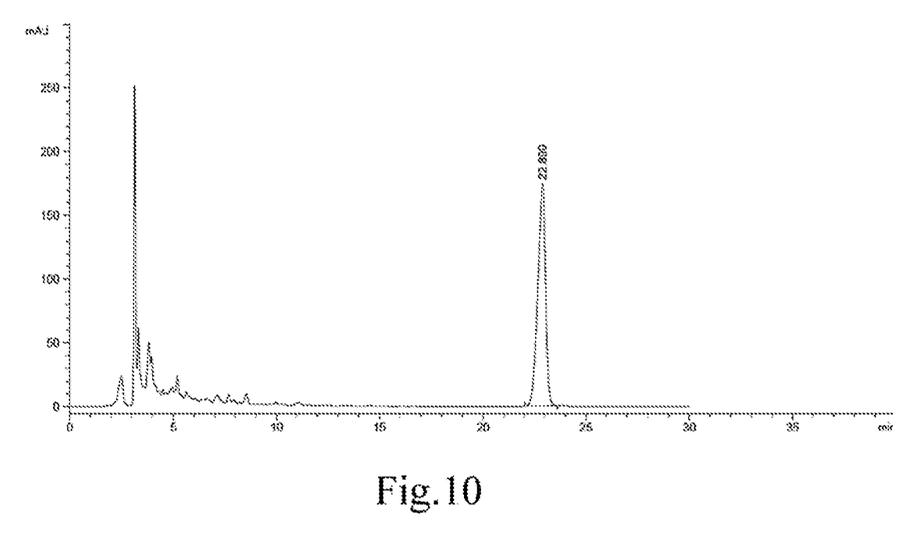
Figure 11:
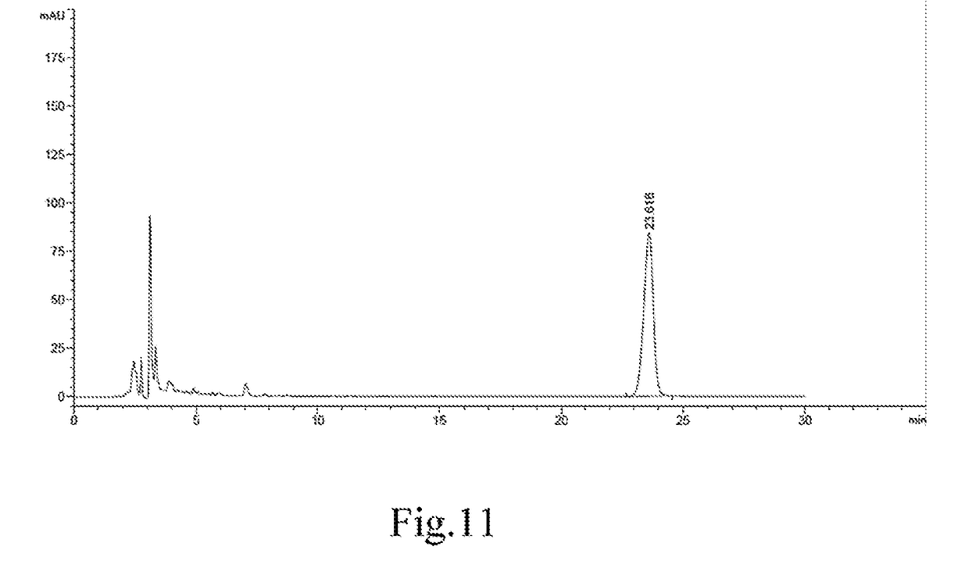
Figure 12:
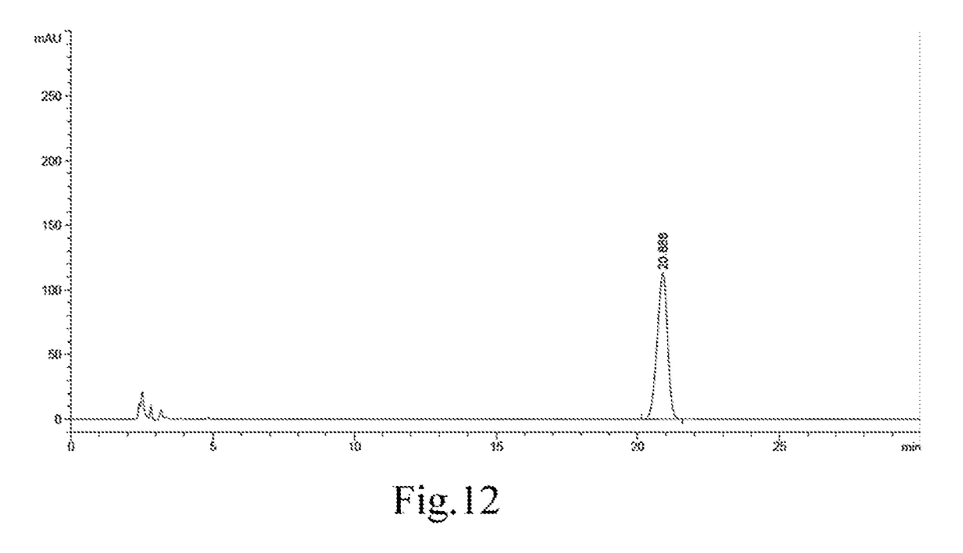

| parameters | Example 1 | Comparative Example 1 | Comparative Example 2 | Comparative Example 3 | Comparative Example 4 |
|---|---|---|---|---|---|
| Raw material (dried leaves)/kg | 1.5 | 1.5 | 1.5 | 1.5 | 1.5 |
| Betanin content in the raw material (HPLC)/% | 5.3 | 5.4 | 5.2 | 5.5 | 5.3 |
| Rubusoside product/g | 77.5 | 65.83 | 63.71 | 66.23 | 71.22 |
| Rubusoside recovery rate/% | 96.61 | 51.08 | 61.52 | 68.52 | 81.88 |
| Rubusoside content (HPLC)/% | 99.1% (FIG. 1) | 60.85% (FIG. 9) | 75.32% (FIG. 10) | 85.35% (FIG. 11) | 91.4% (FIG. 12) |
| Product color | Snow white | Pale yellow | Brownish yellow | Pale yellow | Pale yellow |

INDUSTRIAL APPLICABILITY

The application provides a method for preparing rubusoside. The application obtains rubusoside by raw material crushing, flash extraction, double centrifugations, macroporous resin purification, desorption, enzymatic hydrolysis, organic film decoloring, concentration, crystallization and drying. The application optimizes the quality control of key process such as extraction, separation, purification and decolorization, and can obtain the rubusoside product with purity more than 99%, and the product is white, no bitterness, less solvent residue, no pesticide residue, and stable quality. The product has better economic value and application prospects.

What is claimed is:

1. A method for preparing rubusoside, comprising the steps:
   (1) providing a dry sample of *Rubus suatrssimus S. Lee* leaves, crushing and passing them through 40-60 mesh sieve, putting the obtained powder material into a flash extractor, in which water at the amount of 18-20 times by weight of the powder is added, extracting for 3 times, 1 minute for each time, and combining all extract solutions to get the total extract solution;
   (2) concentrating the total extract solution to a concentrate solution 5 times by weight of the raw leaves, centrifuging the concentrate solution through a disc centrifuge and a tube centrifuge to obtain a centrifugate, and adjusting the centrifugate to pH 5.0-6.0 using an acid solution;
   (3) passing the adjusted centrifugate through a macroporous resin column, adjusting the effluent to pH 7.0 using 0.2% sodium hydroxide solution, detecting the content of rubusoside and ending sample loading when the content is >1%; when the loading is completed, washing the column firstly using pure water until the effluent is colorless and clear, secondly using an alkaline solution until the effluent is PH 11 to 12, thirdly using pure water until the effluent is PH 7.0-7.5, fourthly using an acid solution until the effluent is PH 2.0-2.5, and finally using water until the effluent is PH 7.0;
   (4) desorbing with 45%-50% ethanol solution, collecting the effluent from the time rubusoside is detected as >1% to the time rubusoside is detected as <1%, and concentrating the effluent under reduced pressure to a concentrate solution of 5 Baume Degrees (°Bé);
   (5) adding a biological enzyme to the concentrate solution obtained in step (4), and digesting at a temperature of 45-60° C. for 1-3 hours to obtain an enzymatic hydrolysate;
   (6) passing the enzymatic hydrolysate through an organic membrane of 8000 molecular weight under the inlet pressure of 0.45-0.5 MPa, then through an organic membrane of 800 molecular weight under the inlet pressure of 1.8-2.0 MPa to obtain a decolored filtrate;
   (7) concentrating the filtrate under reduced pressure to obtain a thick paste of 15 Baume Degrees (°Bé), adding methanol or ethanol as a solvent at an amount 3 times that of the thick paste, crystallizing at 5-11° C. for 8-14 hours, drying the obtained crystal to obtain rubusoside.

2. The method according to claim 1, wherein the centrifugation time of the disc centrifuge in step (2) is 30-50 minutes, and the centrifugation time of the tube centrifuge is 40-60 minutes.

3. The method according to claim 1, wherein the alkaline solution in step (3) is selected from a 0.2% aqueous solution of sodium hydroxide or a 0.2% aqueous solution of potassium hydroxide; the acid solution is selected from 0.4% aqueous solution of hydrochloric acid or 0.45% aqueous solution of sulfuric acid.

4. The method according to claim 1, wherein the biological enzyme in step (5) is one or a combination of two or more enzymes selected from the group consisting of bromelain, pectinase and neutral protease.

5. The method according to claim 4, wherein the amount of the added biological enzyme is 0.5‰-1.2‰ of the total weight of the leaves.

6. The method according to claim 5, wherein the amount of the added biological enzyme is 0.6‰-0.8‰ of the total weight of the leaves.

7. The method according to claim 4, wherein the biological enzyme is a combination of pectinase and neutral protease at the ratio of 5:1.

8. The method according to claim 4, wherein the biological enzyme is a combination of pectinase and bromelain at the ratio of 1:1.

9. The method according to claim 4, wherein the biological enzyme is a combination of a neutral protease and bromelain at the ratio of 4:1.

* * * * *